(12) United States Patent
Frisina et al.

(10) Patent No.: US 6,358,479 B1
(45) Date of Patent: Mar. 19, 2002

(54) REACTION BLOCK ASSEMBLY FOR CHEMICAL SYNTHESIS

(75) Inventors: Dominic Frisina; Feng-Guang Rong; Michael R. Ferriell; Hossain Saneii, all of Louisville, KY (US)

(73) Assignee: Advanced ChemTech, Inc., Louisville, KY (US)

( * ) Notice: Subject to any disclaimer, the term of this patent is extended or adjusted under 35 U.S.C. 154(b) by 0 days.

(21) Appl. No.: 09/580,614

(22) Filed: May 30, 2000

(51) Int. Cl.[7] .............................. B01J 19/00; C08F 2/00; G01N 1/00

(52) U.S. Cl. ..................... 422/131; 422/103; 422/104; 422/101; 422/130

(58) Field of Search ................................. 422/131, 130, 422/102, 99, 101, 129, 138, 104; 436/178; 435/4; 210/321.75

(56) References Cited

U.S. PATENT DOCUMENTS

| | | | | |
|---|---|---|---|---|
| 5,609,826 | A | * | 3/1997 | Cargill et al. .................. 422/99 |
| 5,716,584 | A | * | 2/1998 | Baker et al. ................. 422/131 |
| 6,074,613 | A | * | 6/2000 | Harness et al. .............. 422/101 |
| 6,083,682 | A | * | 7/2000 | Campbell et al. ............... 435/4 |
| 6,083,761 | A | * | 7/2000 | Kedar et al. ................. 436/178 |
| 6,117,397 | A | * | 9/2000 | Antonenko et al. .......... 422/101 |
| 6,132,686 | A | * | 10/2000 | Gallup et al. ................ 422/130 |
| 6,159,368 | A | * | 12/2000 | Moring et al. ......... 210/321.75 |
| 6,171,555 | B1 | * | 1/2001 | Cargill et al. ................ 422/104 |
| 6,238,627 | B1 | * | 4/2001 | McGowan et al. .......... 422/130 |
| 6,258,325 | B1 | * | 7/2001 | Sanadi ........................ 422/101 |
| 6,274,091 | B1 | * | 8/2001 | Mohan et al. ............... 422/103 |

* cited by examiner

*Primary Examiner*—Jill Warden
*Assistant Examiner*—Brian Sines
(74) *Attorney, Agent, or Firm*—John E. Vanderburgh

(57) ABSTRACT

The reaction block assembly of the invention comprises a reaction block in which are disposed a plurality of reaction wells. Influent and effluent ducts open at the upper face of the reaction block adjacent each of the reaction wells. These ducts provide communication between each reaction well and a source of reagents and gases and with waste removal means for removal of effluent from the reaction wells. A membrane sheet overlies the upper face of the reaction block to define a pneumatic valve to open and close the duct openings each of the reaction wells to control the input of reagents and gases and effluent flow from the reaction wells. The reaction block assembly preferably includes a temperature control block that underlies the reaction block for control of the temperature in the reaction wells. A waste block underlies the reaction block or, if used, the temperature control block. The effluent ducts from the reaction wells communicate with the waste block for removal of reaction well effluent from the reaction block assembly. Overlying the reaction block is a top manifold plate block for delivery of high pressure gas to actuate the pneumatic valves by applying pressure against the membrane to seal the duct openings.

7 Claims, 4 Drawing Sheets

REACTION BLOCK ASSEMBLY FOR CHEMICAL SYNTHESIS

FIELD OF THE INVENTION

This invention relates to the synthesis of organic and inorganic chemical compounds and more particularly to an improved reaction block assembly for the manual and automated execution of solid and solution phase chemical processes of all types.

BACKGROUND OF THE INVENTION

Discovery of new chemical compounds is at the core of many research and development efforts. A typical discovery research cycle involves multiple steps being conducted in a repetitive fashion. This initiates with the design of an experiment or series of experiments, execution of the experiment(s), analysis and evaluation of the results obtained, followed by design of another experiment or set of experiments. This cycle is repeated until the optimal desired result is attained. Scientists are continually searching for more efficient methods and procedures to aid in their research programs. Recently, the development of combinatorial chemistry concepts has initiated new approaches towards all aspects of the discovery process, in particular synthesis. The basis of combinatorial concepts is to enable the rapid, or high throughput, preparation of many different chemical compounds or formulations of chemical compounds, then investigate them, again in a rapid manner, for a particular desired property. This property could be biological activity, superconductivity, or the ability to catalyze another chemical transformation, as well as many others. The primary goal of combinatorial approaches is to speed up the discovery cycle and thereby result in more rapid achievement of desired results. These approaches, although relatively new, are finding applications in an ever-expanding realm. These efforts are now being directed towards a wide range of scientific fields including, but not limited to, pharmaceuticals, agrochemicals, catalysts, polymers, inorganic materials, flavors, fragrances, cosmetics and even process research.

Towards the realization of combinatorial concepts in practice, a number of tools have been developed to help achieve rapid and efficient processing. Among these are those that have been termed reaction blocks. Although many such devices have been tested, in general all possess some inherent limitations in terms of the reaction processes which can be performed in them. Among these limitations are:

(i) the materials utilized in the device are not compatible with certain chemicals or reaction conditions;

(ii) the reaction block cannot attain the temperatures required for the conduct of the widest variety of chemistry;

(iii) the standard reaction technique called reflux is not supported;

(iv) pressure cannot be created within the reactor as this will cause the contents to prematurely discharge;

(v) gas reagents cannot be utilized;

(vi) cross-contamination can occur between the individual reaction wells within a reactor;

(vii) a great deal of manual manipulation is required in order to properly utilize them in start to finish reaction processing;

(viii) those that are suitable for manual processing are not compatible with fully automated systems;

(viv) many are more suitable for only solution phase or only solid phase chemical processes rather than both;

(x) the physical configuration is not compatible with the requirements of further analytical techniques and the testing procedures utilized;

(xi) recovery of products from the device is not easily achieved or requires additional manual intervention.

Since the realm of potential chemical applications is so broad, a device in which any desired chemical reaction or transformation could be conducted is highly preferable. However, prior to this invention, no reaction block generally applicable to all types of chemical processes has been realized. Generally in order to achieve the rapid sample processing inherent in the conduct of combinatorial approaches, automation is adopted to assist wherever possible with the individual stages of the discovery cycle. However, in chemistry, particularly in synthesis, scientists often prefer to perform initial work manually, or with a minimal amount of automation. This allows them to more closely and immediately control, monitor and observe experimentation, which can often be critical to devising successful results. Once this initial chemistry development is completed, however, the next phases of study, often involving the conduct of larger numbers of experiments, such as syntheses, are most efficiently performed with the aid of automated systems. The ability to be able to directly transfer chemistry from the initial development stage to later stages is greatly enhanced by utilization of the same reaction block technology in each stage. Further, although chemists may wish to employ a reaction block in a manual manner, for some reaction blocks, manual intervention is required in order to utilize them. It would be desirable that this choice be left to the scientist. Preference would be given to a reaction block assembly that could be utilized in both for manual procedures and those involving automation, such as robotics.

For biological evaluation, a particular mechanical configuration has been adopted as a standard, that of the 96 well microplate. It is therefore highly desirable to be able to either conduct chemical experiments that are directed at finding biological activity in this configuration or in a format that can be easily or directly transferred to this configuration. For most other types of chemical investigation, such a standard does not currently exist and a wide variety of analysis configurations are employed. It is therefore also desirable that products can be easily transferred into any other configuration required.

A vast amount of chemical experimentation can be conducted at ambient temperatures and pressures. However, many chemical reactions and transformations and processing steps require extremes of temperature and pressure. In particular, reaction block technology has not been able to provide the ability to conduct reactions under pressure or with gaseous reagents. This is limiting as several very common chemical processes, such as hydrogenation or dissolving metal reductions, require handling of gases. It is desirable that a reaction block be able to operate in and withstand high and low temperatures as well as high and low pressures. Similarly, the ability to perform reflux applications is important. Although the advent of accurate alternative temperature control methods makes the use of reflux unnecessary in many cases, the chemist remains very comfortable with this standard technique and requires that any reactor have an appropriate condenser function to permit its application. This is particularly critical in the solution phase methodologies described later. In testing of chemical materials, as high a degree of purity as can be achieved is typically required for the analysis results to be properly interpreted. Therefore, when a reaction block contains multiple wells for the conduct of individual reactions, cross-contamination between them must be prevented.

Traditional chemistry is conducted by adding materials together in a particular manner which will undergo some type of transformation, typically in a liquid solvent medium. This has also been termed solution phase chemistry. Alternatively, reactions can be conducted at least partially with one or more of the reactants attached to an insoluble polymer support. A number of advantages are conveyed by this type of solid phase process, in particular speed of processing, ability to achieve complete transformation through the use of excess reactants and reagents (which usually result in material of higher purity) and amenability to automation. Indeed, the use of solid phase chemistry helped revolutionize peptide and oligonucleotide research by providing efficient access to synthetic material for research investigations. Likewise, these advantages have made use of solid phase chemistry techniques common in combinatorial approaches. However, not all chemical transformations can be conducted on solid phase, and the familiarity of many chemists with this technique is much lower than the more traditional approaches. It is therefore desirable that a reaction block be able to efficiently conduct both solid and solution phase chemistry.

SUMMARY OF THE INVENTION

The present invention overcomes the foregoing limitations by providing an improved reaction block assembly capable of performing many types of chemical processes, including reactions involving gases and both solid and solution phase chemistries. The reaction block assembly of the present invention further allows for the conduct of chemical reactions, transformation and other processing at a wide range of temperature and pressure. The reaction block assembly includes a reaction block provided with reaction wells. The materials utilized in its construction are chemically inert and compatible with the same range of temperature and pressure. The reaction block assembly of the present invention is designed to avoid the problem of premature discharge of the reaction wells under pressure. Thus, gas reagents can be utilized when required. For reaction blocks with multiple wells, cross-contamination is eliminated. The identical reaction block assembly can be utilized in a manual fashion as well as in semi and fully automated systems. It allows complete start to finish reaction processing when desired. The conduct of both solution phase and solid phase chemical processes is allowed. The reaction block assembly provides for direct transfer of products to any desired format upon conclusion of any given sequence of chemical steps.

More particularly, the block assembly of the invention comprises a reaction block in which are disposed a plurality of reaction wells. Influent and effluent ducts open at the upper face of the reaction block adjacent each of the reaction wells. These ducts provide communication between each reaction well and a source of reagents and gases and with waste removal means for removal of effluent from the reaction wells. A membrane sheet overlies the upper face of the reaction block and as explained in more detail below defines a first pneumatic valve at each of the reaction wells to control the input of reagents and gases and a second pneumatic valve to control effluent flow from the reaction well. The reaction block assembly preferably includes a temperature control block that underlies the reaction block for control of the temperature in the reaction wells. A waste block underlies the reaction block or, if used, the temperature control block. Waste ducts from the reaction wells communicate with the waste block for removal of reaction well effluent from the reaction block assembly.

Overlying the reaction block is a top manifold plate block for delivery of high pressure gas. The high pressure gas is utilized to actuate the pneumatic valves by applying pressure against the membrane to seal the influent duct and the effluent duct openings. Releasing the high pressure allows the pneumatic valves to be opened by relieving the positive pressure on the membrane further assisted by the reverse pressure of the ingredients acted upon by the charging gas introduced into the reaction wells to discharge the fluid contents of the wells. The membrane for opening and closing the pneumatic valves and a septum are disposed between the gas manifold top plate and the upper face of the reaction block. The openings of the reaction wells are closed by caps which are liquid and gas impermeable and they are adapted to be penetrated by a probe for delivery of reagents to the reaction wells. The septum serves to retain pressure in the reaction wells.

The reaction block is composed of a chemically inert, mechanically rigid material capable of being machined. The bottom of each reaction well is individually fitted with an inline filter for accommodation of solid phase chemical resins. The tops of the wells are fitted with caps to minimize contact by chemical vapors between the reaction wells and the septum, thus preventing corrosion of the septum and leaching of materials from the septum. The caps are preferably self sealing to reseal after accepting a probe for the delivery and aspiration of liquid reagents and solvents or aspiration of ingredients from the reaction wells.

DESCRIPTION OF THE PREFERRED EMBODIMENTS

Figure 1:
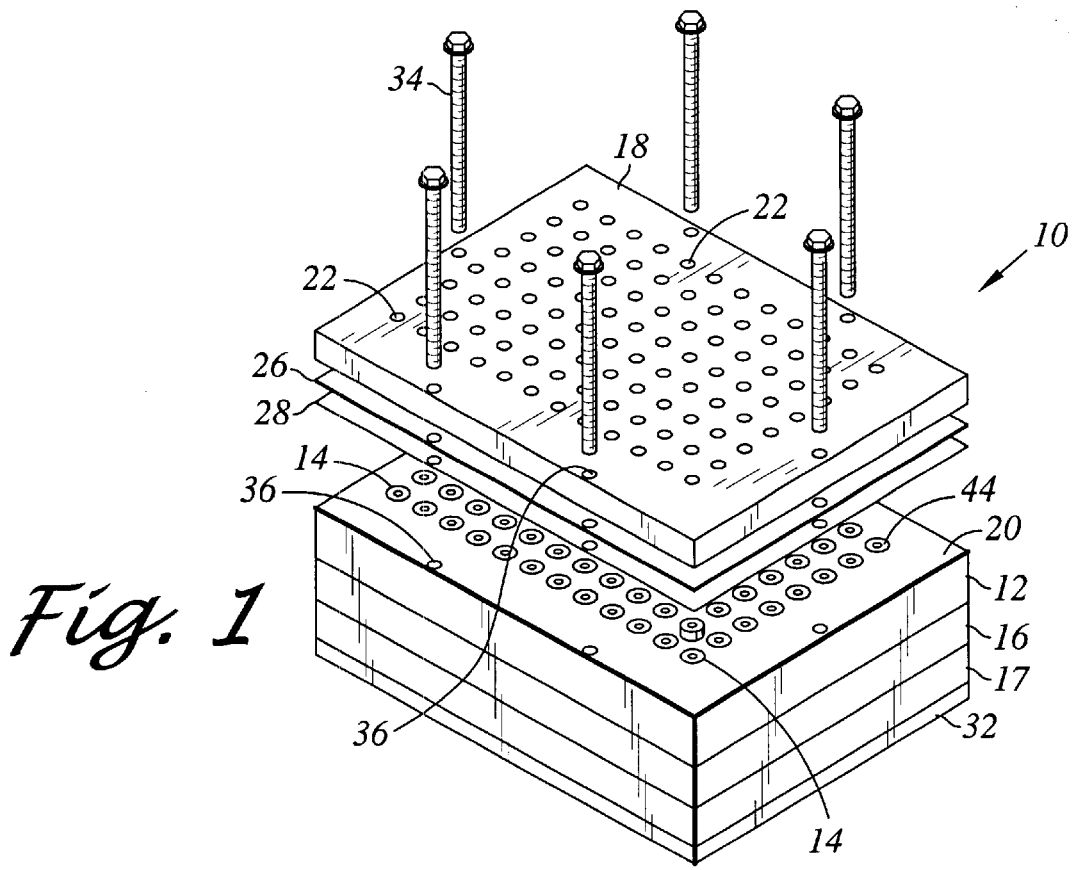
FIG. 1 is a perspective view, exploded, illustrating the reaction block assembly of the present convention.

Referring to FIG. 1, the reaction block assembly of the present invention, shown generally as 10, comprises a reaction block 12 in which are disposed a plurality of reaction wells 14 that, as illustrated, are arranged in a conventional 96 well arrangement. Underlying the reaction block 12 is a temperature control block 16 and a waste disposal block 17. A top manifold plate 18 overlies the upper face 20 of the reaction block 12. A plurality of access ports 22 are provided in the manifold plate 18 and these are arranged in a pattern corresponding to the arrangement of the reaction wells 14 for alignment with the reaction wells when the manifold plate is positioned over the reaction block 12. Disposed between the top plate in 18 and the reaction block 12 is a membrane sheet 28 and a septum sheet 26. The membrane sheet 28 lies over the upper face 20 of the reaction block 12 and the septum sheet 26 lies over the membrane sheet and is protected from contact with reagent chemicals by the membrane sheet. The reaction block assembly 10 is completed by a base plate 32 which underlies the waste block 17. The reaction block assembly 10 is secured by bolts 34 which extend through alignment bolt holes 36 in the top plate 18, the reaction block 12, the temperature control block 16 and the waste block 16 into the base plate 32.

Figure 2:
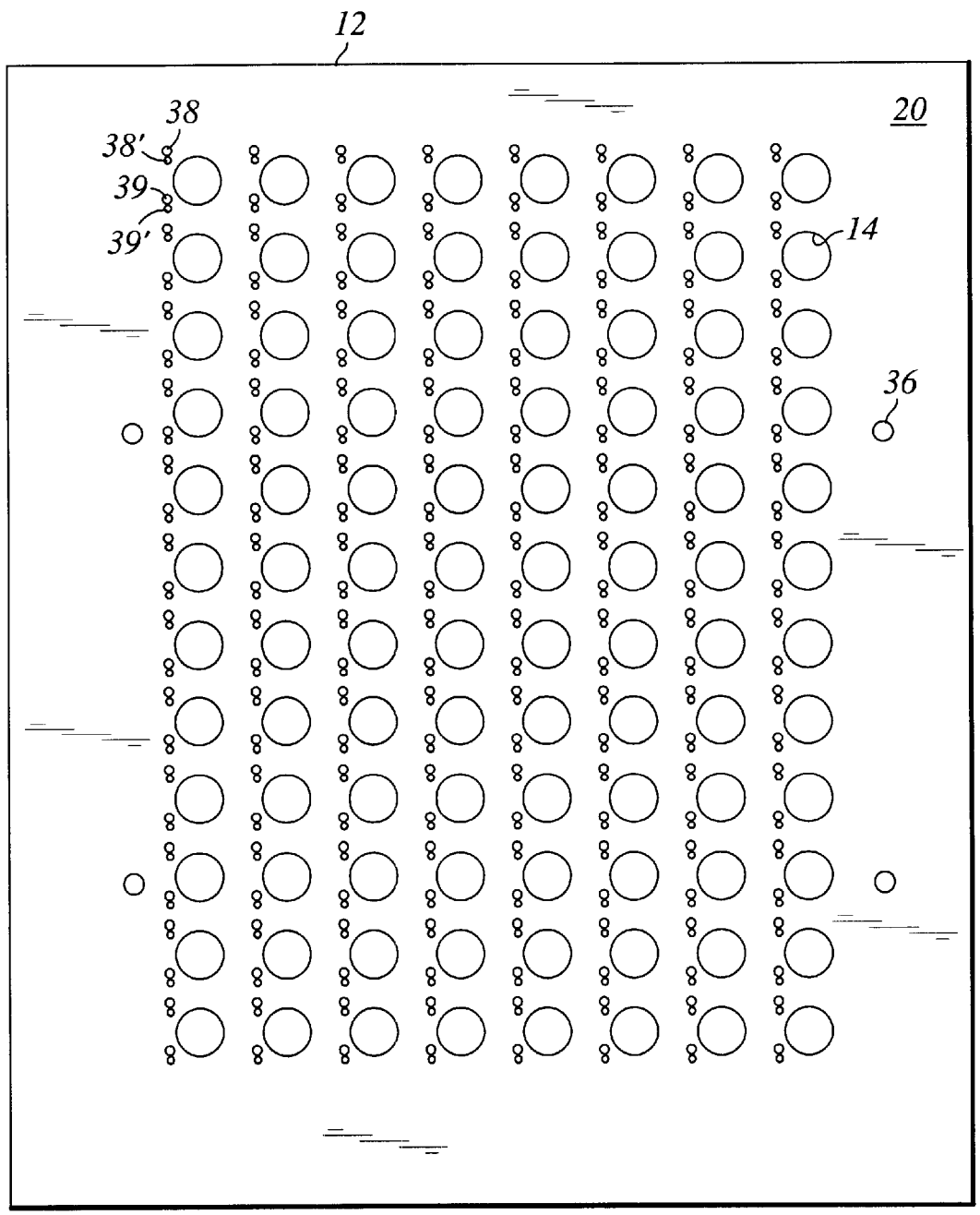
FIG. 2 is a top plan view showing the upper face of the reaction block of the reaction block assembly.

Referring to FIG. 2, the upper face 20 of the reaction block 12 is illustrated showing more clearly the arrangement of the reaction wells 14. The reaction wells 14 open onto the upper face 20 of the reaction block 12 and adjacent each of the openings is a pair of duct openings 38,38' and 39,39' that are opened and closed by the membrane sheet 28 responsive to gas pressure fed through the top manifold plate 18. As most clearly shown in FIG. 3, the area of a upper face 20 immediately surrounding each of the paired duct openings 38,38' and 39,39' is machined to form a valve seat 42 into which a portion of a membrane sheet 28 extends to selectively close the duct opening pairs. The reaction wells 14 are sealed by caps 44. An inverted cone shaped probe duct 45 having its smaller end opening into the reaction well 14 is provided in each of the caps 44 to permit access by a probe into the interior of the reaction wells through the cap 44 for the introduction of solid support and liquid reagents.

Figure 4:
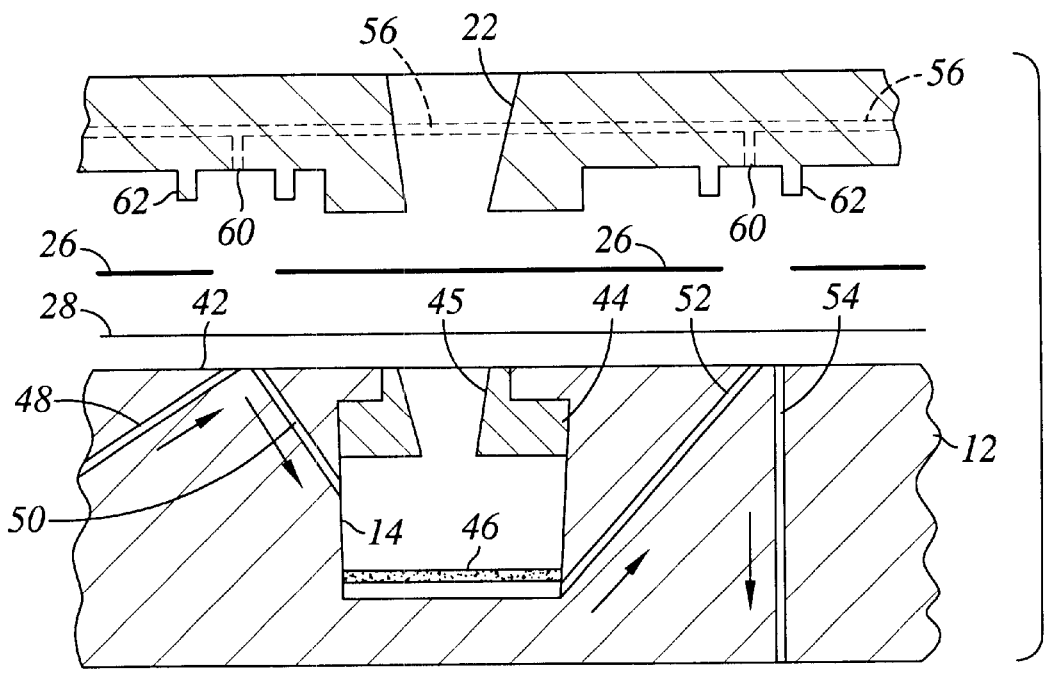
FIG. 4 is a side sectional view broken away for compactness of illustration showing a section of the reaction block assembly illustrating the reaction well and input and output ducts.

As is most clearly shown in FIG. 4, each of the reaction wells 14 defines a reaction chamber having at its lower portion a porous divider 46, such as a sintered glass disk, open cell expanded tetrafluroethylene or other porous material that is inert to the reagents and the reaction conditions, for retention of the solid support and coupled product while permitting liquid to pass through the porous material. A first inlet duct 48 communicates between a source of inert or reagent gas (not shown) and the upper face 20 of the reaction block 12 through a duct opening 38. A second inlet duct 50 communicates with the reaction in well and opens at 38' adjacent the duct opening 38. A first discharge duct 52 opens in into the bottom of the reaction chamber 14 and at the duct opening 39 in the upper face 20 of the reaction block 12. A second discharge duct 54 extends from duct opening 39' to the waste disposal block 17. The area surrounding the paired duct openings 38,38' and 39,39' defines the valve seat 42. The valve seat 42 is an area of the upper face 20 of the reaction block 12 where the paired duct openings 38,38' and 39,39' are located that is machined to a smooth finish so as to allow the flexible membrane 28 to form a tight seal over the paired duct openings. It will be understood, however, that the surface may be machined as a slight depression for insertion of that portion of the membrane sheet 28 overlying the paired duct openings.

Figure 3:
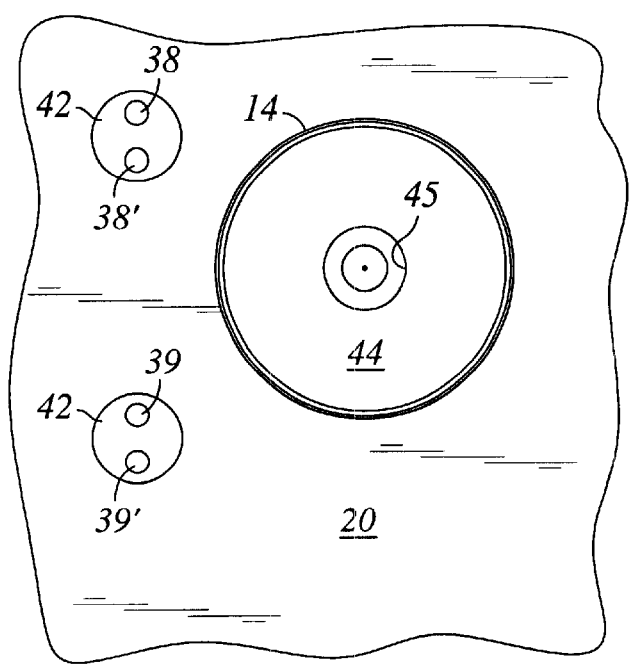
FIG. 3 is an enlarged view of a portion of the upper face of the reaction plate.

As can be seen from FIG. 3, the duct openings 38,38' of the inlet ducts 48 and 50 are located adjacent one another in closely spaced relationship to normally permit fluid communication between the first and second inlet ducts. Similarly, the duct openings 39,39' of the first and second discharge ducts 52 and 54 are also closely spaced for fluid communication between them. The flexible membrane sheet 28 overlies the upper face 20 of the reaction block, including each of the paired duct openings 38,38' and 39,39' and serves as the pneumatic valve to selectively open and close the duct opening pairs responsive to the urging of high-pressure gas. The membrane sheet 28 is formed from a chemically inert, flexible material such as skived sheets of Teflon®.

Figure 5:
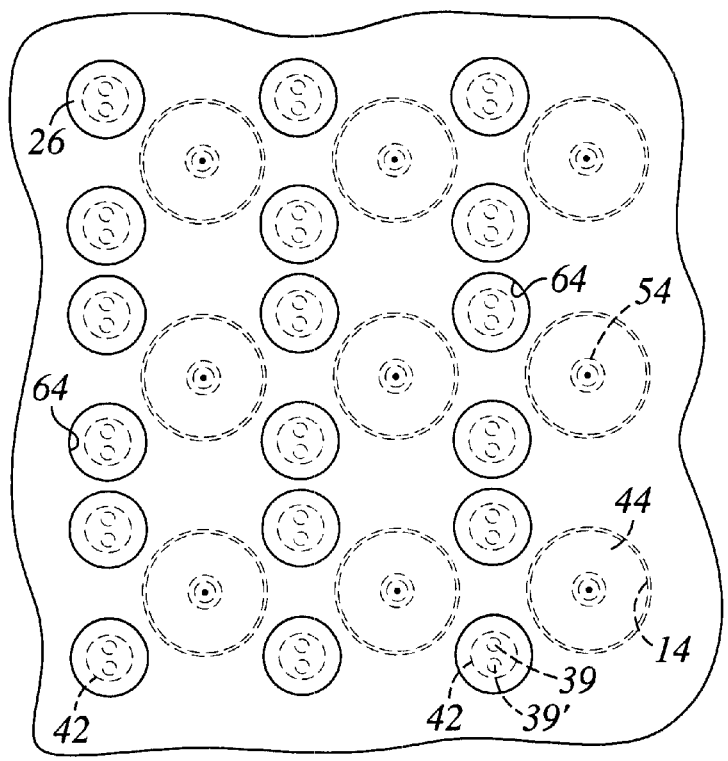
FIG. 5 is a plan view of a septum utilized in the reaction block assembly.

As seen in FIG. 5, the septum sheet 26 overlies the membrane sheet 28 and serves as a gasket between the reaction block 12 and the top manifold plate 18. The septum sheet 26 is formed of a rubber like material such as highly plasticized polyethylene or polypropylene and is provided with including a plurality of openings 64 corresponding in number and arrangement to the duct openings 38,38' and 39,39' to permit access by high-pressure gas to the portions of the membrane sheet 28 overlying the paired duct openings to activate the valves. However, the septum sheet 26 seals the openings to the reaction wells 14 and, once clamped between the reaction block 16 and the top manifold plate 18, the septum sheet cooperates with the caps 44 to maintain pressure within the reaction wells. The septum sheet 26, being formed of a rubber like material, allows for the penetration by a probe and is re-sealable when the probe is withdrawn. The septum sheet 26 is protected from attack by the reagents utilized in the synthesis by the chemically inert membrane sheet 28.

Figure 6:
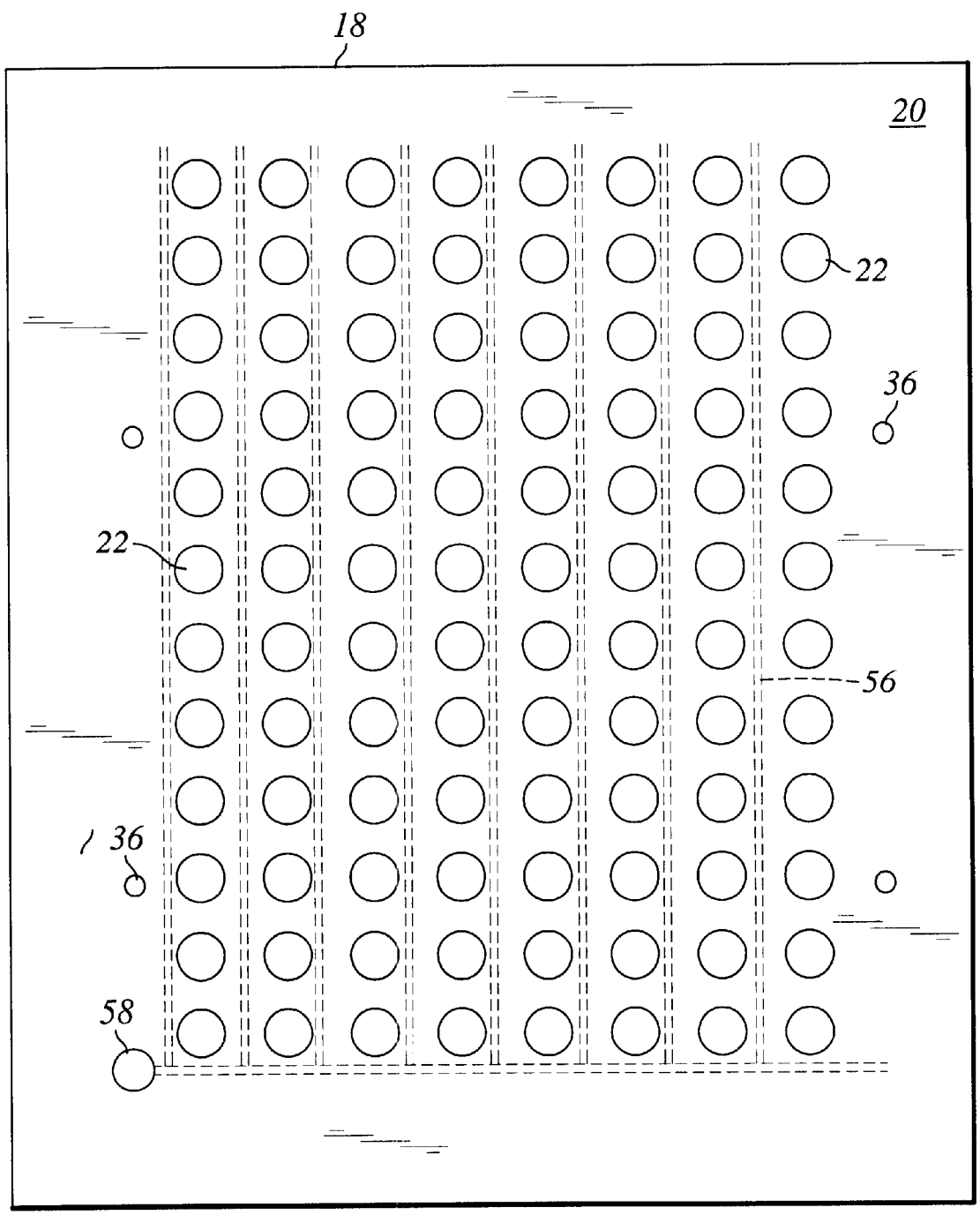
FIG. 6 is top plan view of the top manifold plate of the reaction block assembly.

As shown in FIG. 4 and FIG. 6, the top manifold plate 18 is provided with manifold passages 56 that communicate with a source of high-pressure gas through a manifold gas input port 58. Ports 60 opening on the lower surface of the manifold plate 18 are aligned with each of the manifold passages 56 and each of the duct outlets 38,38' and 39,39' direct the high pressure gas to activate the membrane sheet 28 for closing the duct openings. In the preferred embodiment, a downwardly extending annular member 62 is formed on the lower surface of the manifold plate 18 to surround the openings of the ports 60. The annular member 62, when assembled on the reaction block assembly 10, clamps against the upper face 20 of the reaction block 12 to secure a portion of the membrane sheet 28 around the valve seats 42 and the duct openings 38,38' or 39,39'. The membrane sheet is securely clamped about the valve seat 42 while at the same time the portion of the membrane sheet over the duct openings 38,38' or 39,39' is able to flex between an open and closed position. In this manner gas pressure is maintained against the membrane sheet 28 when the duct openings 38,38' or 39,39' are selectively closed by the membrane sheet. The probe access ports 22 are arranged on the manifold plate 18 to correspond with the openings to the reaction wells 14 in the reaction block 12. The access ports 22 are configured to permit the extension there through of a probe for insertion into the reaction wells 14.

In operation, a solid support, such as resin beads, and liquid reagents are introduced into the reaction wells 14 of the reaction block 12. Although they may be introduced manually it is preferred to introduce them by means of probes through the access ports 22. The reaction wells 14 are then normally sealed by the caps 44. Inert and reagent gases are introduced to the chamber of the reaction wells 14 through the inlet ducts 48 and 50. During the introduction of inert or reagent gases to reaction wells 14 the flow of high-pressure gas is discontinued allowing the membrane sheet 28 to move to an open position away from the duct openings 38,38' and 39,39' to permit fluid communication between the ducts. In this manner the pneumatic valves are in the open position and flow into the reaction wells 14 can occur. Reagent gas flow is preferably produced by a low-pressure inert gas introduced at the source of reagent gas. However, sufficient negative pressure may be imposed through the manifold plate 18 to draw the reagent gases into the reaction wells 14 from the source of reagent gas.

When the reaction wells 14 are charged with reagent, a high-pressure gas is caused to flow through the manifold passages 56 and the ports 60 to contact the membrane sheet 28 over the duct openings 38,38' and 39,39' and urge the membrane sheet into a closed valve position to seal the duct openings. Pressure is maintained during the reaction step and upon completion of the reaction, the flow of high-pressure gas is discontinued. The manifold plate 18 is vented to release the pressure on the membrane sheet 28 allowing it to return to its normally open position unsealing the duct openings 38,38' and 39,39'. A low-pressure inert gas is introduced into the reaction wells 14 to force the liquid components in the wells through the porous divider 46 into the first and second discharge ducts, 52 and 54, to the waste disposal block 17. Following the reaction step, the components of the reaction wells 14 may be subjected to one or more washing steps and the washing solutions may be introduced and removed in the same manner as described for the reagents or introduced directly into the reaction wells by a probe. The number of reaction and washing steps is not limited and may be repeated a number of times depending upon the nature of the compound being formed on the solid support. Upon completion of the reaction and washing steps, the compound is cleaved from the solid support by the introduction of cleaving agents according to procedures well understood in the art. Once cleaved from the solid support, the finished product will pass through the porous divider 46 and can be discharged and collected through the waste disposal blocked 17 or in the alternative can be drawn out of the reaction wells by a probe for transfer to a suitable collection point.

The reaction block assembly 10 is adaptable for a variety of procedures for the synthesis of chemical compositions. For example, the temperature control block 16 may be used to control the temperature within the reaction wells. Thus reactions may be carried out at temperatures above and below room temperature.

Although the operation of the reaction block assembly 10 has been described in connection with solid phase reaction it will be understood that solution phase synthesis reactions are carried out with good results. The operation of the reaction block assembly 10 is essentially the same for solution phase synthesis as for the above-described solid phase synthesis.

The reaction block assembly 10 is particularly suited for carrying out reactions under elevated pressure. The combination of the sealing caps 44 and the overlying septum sheet 26 acts to provide a pressure tight seal for the reaction wells 14. In addition, the membrane sheet 28 seals the duct openings 38,38' and 39,39' to prevent loss of pressure through the inlet ducts 48 and 50 and the discharge ducts 52 and 54. Pressure may be introduced to the reaction wells 14 by a probe.

The reaction block assembly 10 is particularly suited for automated chemical synthesis procedures and, as mentioned above, the arrangement of reaction wells in the reaction block is preferably a 96 well configuration which is the conventional titer plate configuration utilized in many robotic instruments. It will be understood, however, that the arrangement and the number of reaction wells in the reaction block assembly 10 is a matter of choice depending upon the type of reaction and the synthesis procedure being utilized. The reaction block assembly 10 can be used in semi automated and manual synthesis operations as well as in automated synthesis operations.

As will be understood by those skilled in the art, various arrangements which lie within the spirit and scope of the invention other than those described in detail in the specification will occur to those persons skilled in the art. It is therefore to be understood that the invention is to be limited only by the claims appended hereto.

Having described the invention, we claim:

1. A reaction block assembly for the synthesis of chemical compounds comprising:
   a. a reaction block defining an upper surface, a plurality of reaction wells formed therein, said wells opening to said upper face of said reaction block;
   b. each said reaction well having at least a first and a second inlet duct opening at said upper face of said reaction block adjacent said reaction well opening to define paired duct openings for communication between said first and said second duct, said first inlet duct communicating with a source of reagent fluid and said second inlet duct communicating with the interior of said reaction well;
   c. each said reaction well having at least the first and a second discharge duct each opening at said upper face of said reaction block adjacent said reaction well opening to define paired duct openings for communication between said first and said second discharge duct, said first discharge duct communicating with said reaction well and said second discharge duct communicating with waste disposal means for the removal of fluids from said reaction well;
   d. a manifold plate having a lower surface overlying said upper face of said reaction block, said manifold plate being in communication with a source of high-pressure gas and having manifold passages for conveying said gas throughout said manifold plate, each said manifold passage having a plurality of ports which open at the lower surface of said manifold plate in substantial alignment with corresponding paired duct openings when said manifold plate is assembled on said reaction block;
   e. an inert membrane sheet overlying said upper surface of said reaction block and a septum sheet overlying said membrane sheet; said membrane sheet and said septum sheet being clamped between said manifold plate and said reaction block
   f. means for securing said manifold plate and said reaction block in clamping relationship;
   whereby high-pressure gas is caused to flow through said manifold passages and said charging ducts to assert pressure on said membrane forcing said membrane against each of said paired duct openings to seal said openings and to prevent reagent fluid from entering or leaving said reaction wells and maintaining pressure within said reaction wells.

2. The reaction block assembly of claim 1 further including a temperature control block underlying said reaction block for control of the temperature in said reaction wells.

3. The reaction block assembly of claim 1 wherein said membrane sheet defines a first pneumatic valve adjacent each of said reaction wells to controls input reagents and a second pneumatic valve to control effluent flow from said reaction well.

4. The reaction block assembly of claim 1 wherein said waste disposal means comprises a waste disposal block underlying said reaction block.

5. The reaction block assembly of claim 2 wherein said waste disposal means comprises a waste disposal block underlying said temperature control block.

6. The reaction block assembly of claim 1 wherein said ports of said manifold passages communicate between said manifold passages and said membrane sheet overlying each of said duct outlets to direct the high pressure gas against said membrane sheet for closing said duct openings.

7. The reaction block assembly of claim 1 wherein a plurality of downwardy extending annular members corresponding in number and arrangement to said paired duct openings are formed on said lower surface of said manifold plate in surrounding relationship to the openings of said ports, said annular members clamp against said upper face of said reaction block to secure a portion of said membrane sheet around said paired duct openings.

* * * * *